United States Patent
Smith

(10) Patent No.: US 8,021,337 B2
(45) Date of Patent: Sep. 20, 2011

(54) EXPANDABLE SURGICAL PORTAL

(75) Inventor: Robert C. Smith, Middletown, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 31 days.

(21) Appl. No.: 12/519,616

(22) PCT Filed: Feb. 15, 2008

(86) PCT No.: PCT/US2008/002073
§ 371 (c)(1),
(2), (4) Date: Jun. 17, 2009

(87) PCT Pub. No.: WO2008/103306
PCT Pub. Date: Aug. 28, 2008

(65) Prior Publication Data
US 2009/0312710 A1 Dec. 17, 2009

Related U.S. Application Data

(60) Provisional application No. 60/902,737, filed on Feb. 21, 2007.

(51) Int. Cl.
*A61M 5/178* (2006.01)
(52) U.S. Cl. .................................................. 604/164.03
(58) Field of Classification Search ............ 604/164.03, 604/164.01, 164.1, 67, 264, 104, 506; 623/1.12, 623/1.25, 1.15; 606/185
See application file for complete search history.

(56) References Cited

U.S. PATENT DOCUMENTS

| 5,674,240 | A | 10/1997 | Bonutti et al. |
| 5,814,073 | A | 9/1998 | Bonutti |
| 5,944,691 | A | 8/1999 | Querns et al. |
| 6,080,174 | A | 6/2000 | Dubrul et al. |
| 6,183,443 | B1 * | 2/2001 | Kratoska et al. ......... 604/164.03 |
| 6,388,043 | B1 | 5/2002 | Langer et al. |
| 2003/0216804 | A1 | 11/2003 | DeBeer et al. |
| 2004/0087968 | A1 | 5/2004 | Core |
| 2004/0236400 | A1 | 11/2004 | Edwin et al. |

FOREIGN PATENT DOCUMENTS

| EP | 1 454 590 A1 | 9/2004 |
| WO | 03/011154 A2 | 2/2003 |

OTHER PUBLICATIONS

International Search Report for PCT/US2008/002073—date of mailing is Jul. 15, 2008 (1 page).
Extended International Search Report corresponding to European Application No. EP 10 25 0720.9, completed Jul. 19, 2010; mailed Feb. 11, 2009; 6 pages.

* cited by examiner

*Primary Examiner* — Nicholas D Lucchesi
*Assistant Examiner* — Brooke Matney

(57) ABSTRACT

Systems, kits, and methods for establishing percutaneous access are described. A system typically includes a deformable variable diameter cannula sleeve (DVDCS) and a guidewire. The DVDCS will generally have two states, an initial, un-activated condition and a second, activated condition, brought about and controlled under the discretion of the operator. The methods comprise creating an initial access point and tissue tract with a needle, positioning a guidewire through the initial tissue tract, passing the deformable variable diameter cannula sleeve over the guidewire through the tissue tract to a target blood vessel or cavity, and activating the DVDCS to effect radial deformation of the surrounding tissue. Use of the DVDCS reduces the risk of injuring tissue surrounding the tissue tract by lessening the axial forces imparted to the tissue. Kits comprise at least one deformable variable diameter cannula sleeve together with instructions for use.

17 Claims, 10 Drawing Sheets

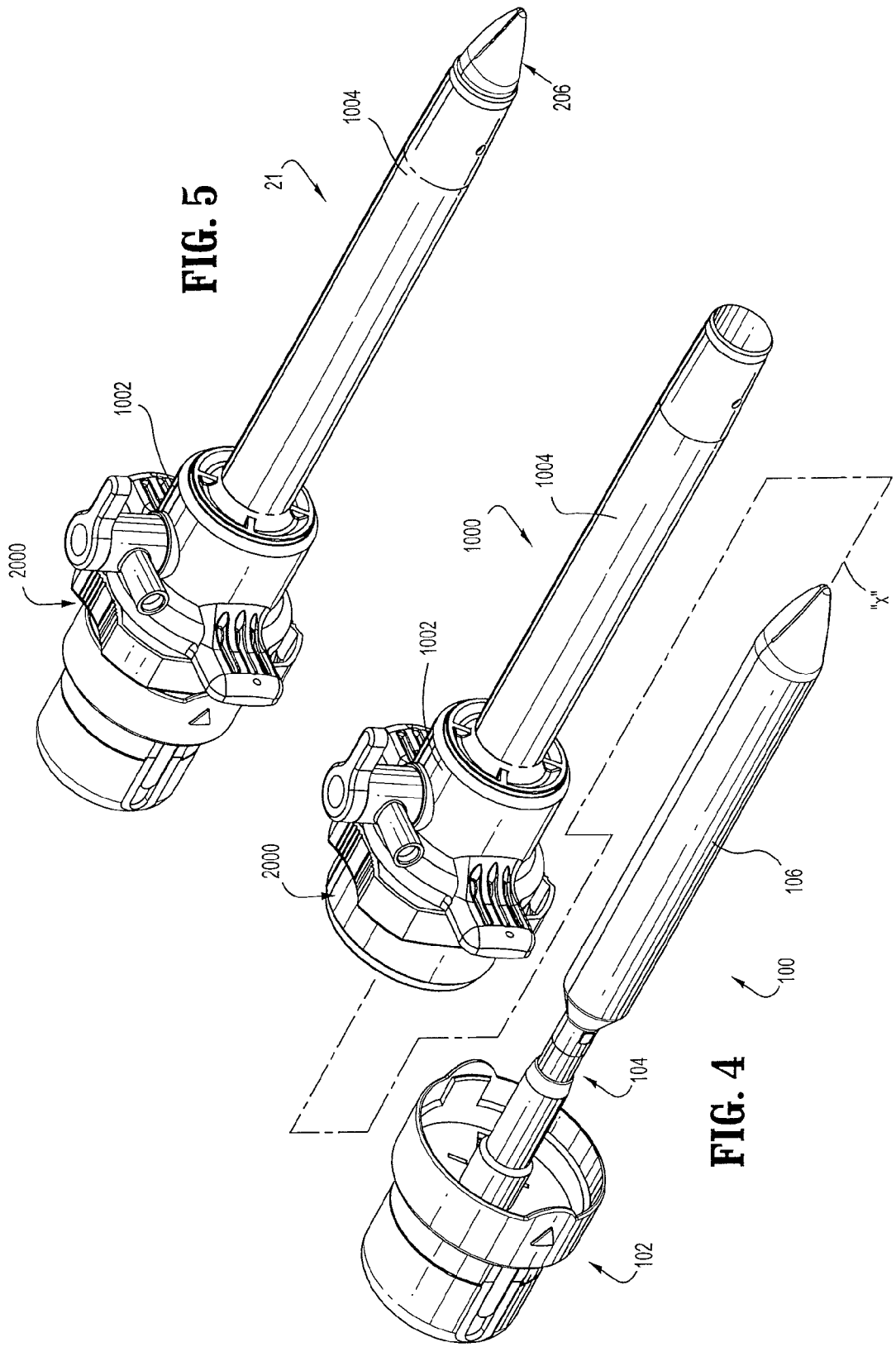

EXPANDABLE SURGICAL PORTAL

CROSS REFERENCE TO RELATED APPLICATIONS

This application is a National Stage Application of PCT/US2008/002073 filed Feb. 15, 2007 under 35 USC §371 (a), which claims priority of U.S. Provisional Patent Application Ser. No. 60/902,737 filed Feb. 21, 2007 the entire contents of which are hereby incorporated by reference.

BACKGROUND OF THE INVENTION

Field of the Invention

The present disclosure relates generally to medical devices and medical methods. In particular, the present disclosure relates to systems, kits, and techniques for establishing percutaneous access.

a. Vascular Access

Percutaneous access to a patient's vasculature is necessary for a wide variety of diagnostic and therapeutic purposes. Of interest to the present disclosure, the most common method for accessing a patient's blood vessel is the Seldinger technique. While a wide variety of variations exist, generally, in employing the Seldinger technique, the surgeon initially accesses a target blood vessel with a needle creating an access point and a tissue tract. Next, the surgeon will pass a guidewire through the needle into the tissue tract, withdraw the needle over the guidewire, pass a dilator over the guidewire to enlarge the diameter of the tissue tract so that it can accommodate a larger introducer sheath, and finally, insert the introducer sheath into the newly dilated tissue tract. Once the introducer sheath is in place, access to the blood vessel can be reliably obtained through the lumen it describes.

b. Laparoscopic Access

In laparoscopic procedures, it is often necessary to employ instrumentation through the use of a small, temporary pathway to a surgical site in an effort to access an internal cavity, in particular, the abdominal cavity. Generally, in such procedures, the target cavity is first insufflated. Thereafter, access is created through a puncture site created using a trocar assembly and an obturator removably inserted through the lumen of a cannula. After removal of the obturator, the cannula remains in the cavity, thereby facilitating access through the lumen.

c. Current State of the Art and Problems Addressed by the Invention

With the introduction of a greater number and variety of intravascular and laparoscopic techniques, a need has arisen to provide relatively large diameter access to the vasculature and internal cavities. Accordingly, there is an increased need for instrumentation which can provide access for such medical devices safely, efficiently and reliably.

Additionally, it has long been desirable to provide access systems that are readily insertable into the body and easily advanced, while also being effectively anchorable. Conventional access devices and systems, such as trocar assemblies, frequently become dislodged during use, particularly during extended procedures. This dislodging can cause numerous complications including loss of pneumoperitoneum, required re-insufflation and re-puncture, all of which are time consuming and unnecessarily traumatic for the patient.

Accordingly, the importance and applicability of radial tissue expansion is also growing. Radial tissue expansion serves not only to provide internal access for larger instruments, but to stretch and compress the surrounding tissue, thereby securely anchoring instruments and substantially decreasing the likelihood of dislodged instrumentation.

The art is replete with medical dilating devices such as catheters and cannuli that generally employ individual dilating elements or members to expand puncture sites. With respect to medical dilating apparatus, U.S. Pat. Nos. 5,112,308 and 5,183,464 disclose devices used to enlarge percutaneous penetrations employing expansion members inserted into cannuli. U.S. Pat. No. 5,961,499 discloses a surgical cannula which may be expanded upon the introduction of an inserting member or through the introduction of fluid pressure.

U.S. Pat. Nos. 5,814,058, 5,431,676, 5,183,464 and 6,080,174 disclose the use of radially expanding dilators for accessing non-vascular body locations, all of which are commonly assigned with the present application and the full disclosures of which are incorporated herein by reference.

There exists a need in the art for a device that is readily insertable into the body and easily advanced, while also being effectively anchorable and capable of achieving predetermined dimensions without the employ of additional elements, dilating or otherwise.

It would therefore be desirable to provide improved systems, kits, and methods for establishing percutaneous vascular and laparoscopic access for catheterization and other procedures. In particular, it would be desirable to provide access techniques which could enlarge a percutaneous tissue tract with minimum trauma to surrounding tissue. Such techniques should be suitable for forming large, as well as small diameter access channels. It would be further desirable if the improved systems, kits, and methods were adapted to dovetail with existing techniques, methods and systems for establishing vascular and laparoscopic access. At least some of these objectives will be met by the apparatus and method described hereinafter.

SUMMARY

The present disclosure provides improved systems and methods for establishing percutaneous access to a patient's vasculature and body cavities. Access can be established with respect to a variety of blood vessels including arteries and veins such as the femoral artery, radial artery, and the like, as well as to internal cavities, such as the abdominal cavity, for diagnostic or therapeutic purposes.

In particular, the present disclosure relates to a surgical portal which includes an elongate portal member adapted to provide access to an underlying tissue site through percutaneous introduction. The elongate portal member of the present disclosure defines proximal and distal ends, a longitudinal axis and an axial lumen adapted for the reception of a surgical object. The elongate portal member includes at least one radially deformable portion incorporating a shape memory material adapted to move from an initial condition to an activated condition having first and second radial dimensions, respectively, upon the introduction of an external stimulus, such as heat, electricity, or a magnetic field, as described below.

The methods of the present application comprise particular improvements over the aforementioned Seldinger technique through the employ of a deformable variable diameter cannula sleeve (DVDCS) used to deform an initial needle penetration to access a target blood vessel or cavity. As set forth in the Background section, use of a traditional dilator assembly directly within a tissue tract can subject the tissue to significant axial forces which can delaminate or otherwise damage the surrounding tissue.

The present apparatus and method reduce the risk of such injury by obviating the need for an individual dilating element or member, introducing instead the DVDCS disclosed herein using otherwise conventional techniques. The DVDCS will typically be immobilized (typically being manually held) relative to the tissue tract created during the initial needle penetration so that distal advancement of the DVDCS will impart little or no axial force to the surrounding and underlying tissue. Instead, the tissue will experience primarily radial forces transmitted through the DVDCS upon deformation, as described below.

The DVDCS disclosed herein may be used in vascular as well as laparoscopic applications. The DVDCS may be outwardly or inwardly deformable dependent upon the particular application and whether the surgical instrument to be inserted therein has a larger or smaller diameter than that of the DVDCS in the initial, un-activated condition.

Initially, that is prior to any radial deformation, the DVDCS is in an un-activated state where the DVDCS will have a lumen sized for introduction over a guidewire, as described above and known in the art, the guidewire having a preselected diameter generally constant over its entire length. The guidewire diameter will be relatively small, typically being either 0.36 mm (0.014 in.) or 0.89 mm (0.035 in.), as is conventional in the art. Accordingly, the lumen of the DVDCS, when in its un-activated state, will typically be sized in the range of 0.46 mm (0.018 in.) or 1 mm (0.4 in.) for each of the guidewire sizes mentioned above, i.e. slightly greater than the outside diameter of the guidewire with which it is to be used. At the appropriate time, the surgeon or operator will activate the DVDCS, causing radial deformation, as described below. When activated, the DVDCS will deform, changing dimensions such that the tissue tract will achieve particular dimensions. It is contemplated that the DVDCS, in its activated, deformed state, may exhibit a diameter in the range of 0.5 mm to 15 mm or larger, dependent upon the application in which it is employed.

In one embodiment, the DVDCS will be used to enlarge an initial access point and tissue tract created using otherwise conventional techniques, as described above, in preparation for the insertion of various medical instruments.

The DVDCS of the present application is formed, either wholly or in part, of a material exhibiting mechanical memory properties, such as a shape memory alloy (SMA). SMAs are metals that exist in two distinct solid phases, referred to as Martensite and Austenite. Martensite is relatively soft and easily deformed, whereas Austenite is relatively stronger and less easily deformed. SMAs can be induced to change phase through the introduction of an external stimulus such as, for example, heat, an electrical current or a magnetic field.

Upon exposure to such an external stimulus, it is contemplated that the DVDCS will begin to either increase or decrease in diameter, dependent upon the application in which it is used, as described above, until predetermined dimensions are realized. As the DVDCS will increase or decrease in diameter "automatically", that is, without any mechanical manipulation and merely through the introduction of an external stimulus, the need for an individual dilating or expansion member is eliminated. Consequently, the need to apply substantial axial force in an effort to distally advance such a dilating member through the lumen of a sheath or sleeve into a puncture site is also obviated, thereby substantially limiting the trauma suffered by the patient during the procedure.

It is contemplated that the mechanical memory material incorporated in the application of the present disclosure may include, but is not limited to, the titanium-nickel alloy disclosed in U.S. Pat. Nos. 3,174,851 and 3,672,879, and the titanium-nickel-cobalt alloy disclosed in U.S. Pat. No. 3,558,369. It is further contemplated that the mechanical memory material may include a ferromagnetic shape memory alloy, as described in U.S. Pat. No. 7,104,056, or a two-way shape memory material, as described in U.S. Pat. No. 5,037,427.

The aforementioned titanium-nickel alloy consists essentially of from 52-56% nickel by weight and correspondingly from about 48-44% titanium by weight, the alloy having the structure of a substantially TiNi phase from about 500° C. to about −75° C. This material is originally formed with restraint and by heat annealing (typically 950° to 1,100° F.) into the shape desired once it is inserted into the body (such as a curve, angle, or any other of an infinite variety of single or multiple configurations). Then the material is deformed at a temperature (typically room temperature) below its transitional temperature (from 32° to 331° F.) depending upon relative composition, but typically from 98° to 125° F.) into a shape facilitating easy insertion into the body (such as a straight rod), and the material is incorporated into the electrode, catheter, or the like. After insertion into the body and advancement to the target site, the material is heated to its transitional temperature thereby returning the material to its original shape.

The titanium-nickel-cobalt alloy disclosed in U.S. Pat. No. 3,558,369 has the formula $TiNi_x Co_{1-x}$ wherein Ti denotes titanium and constitutes approximately 50 atomic % of the composition, and the term $Ni_x Co_{1-x}$ denotes nickel and cobalt respectively and make up the remaining approximately 50 atomic percent of the composition x is a factor which varies from greater than 0 to less than 1 whereby the relative percentage of nickel and cobalt varies inversely from less than 100 percent to more than 0 percent. The transitional temperature of this alloy can be varied depending upon relative composition from −396° to +331° F. Otherwise, it is essentially the same as the abovementioned titanium-nickel alloy.

The ferromagnetic shape memory alloy referenced above and described in U.S. Pat. No. 7,104,056 is a smart material that can undergo large reversible deformations in an applied magnetic field. Compared to temperature driven shape memory alloys, the magnetic control offers faster response, as the process of heating, and especially cooling, is slower than applying the magnetic field. At the moment, the largest magnetic field induced deformations have been observed in Ni—Mn—Ga alloys close to the stoichiometric composition Ni2MnGa, where strains up to 6% are obtained in the field of 0.6 T.

The two-way shape memory material described in U.S. Pat. No. 5,037,427 discloses a SMA with a transformation temperature above which the alloy is deformed into a shape memorized in advance. In the two-way shape memory alloy, the alloy can be freely deformed for the memory purpose at a temperature lower than the transformation temperature. The shape thus memorized is exhibited at a temperature higher than the transformation temperature. It should be noted that the alloy continues to keep its shape even after the temperature is lowered below the transformation temperature. Two-way shape memory alloys may also permit the memorizing of a shape at a temperature lower than the transformation temperature with the result that two different shapes can be reversibly exhibited with a boundary set by the transformation temperature.

In one embodiment, it is contemplated that the DVDCS will be heat-activated. In this embodiment, the heat may be transmitted directly to the DVDCS through, for example, the introduction of a heat probe, or indirectly, through connection to an electrical source of sufficient magnitude to heat the DVDCS to its transitional temperature. In either circumstance, once heated to its transitional temperature, the DVDCS will thereafter maintain its original shape even when cooled below its transitional temperature. This embodiment, therefore, is easy to operate and can be readily designed to fit a wide variety of applications.

In one embodiment, the heat-activated mechanical memory material will have a transitional temperature substantially approximate to that of the patient's body such that upon insertion, the DVDCS will deform and achieve the desired dimensions.

It is contemplated that the degree of deformation exhibited by the DVDCS upon activation will vary in proportionate relation to temperature. Accordingly, in this embodiment, at different temperatures, the DVDCS will exhibit varying degrees of deformation such that a particular degree of deformation may be achieved by adjusting the temperature of the DVDCS vis-à-vis the applied magnitude of the external stimulus.

Alternatively, where the SMA comprising the deformable portion of the DVDCS is a ferromagnetic shape memory alloy, it is contemplated that the desired deformation may be triggered through the introduction of a magnetic field.

In one embodiment, the DVDCS may be used to establish percutaneous vascular access. In this embodiment, a blood vessel will be accessed by a needle, through which a guidewire will be passed, as described above. Thereafter, the needle will be withdrawn over the guidewire, at which time the DVDCS of the present invention will be introduced. The DVDCS will be inserted into the puncture, in its un-deformed state, over the guidewire. After insertion, the DVDCS will be deformed through the introduction of an external stimulus, as described above, so as to increase the dimensions of the puncture site and facilitate access by a surgeon.

In an alternative embodiment, the DVDCS disclosed herein may be used in cooperation with a trocar assembly. Trocar assemblies typically include an obturator which is removably inserted through a cannula. In this particular application, the DVDCS will be the vessel through which the obturator is inserted. The obturator may include a safety shield which protects against unintentional puncturing by the sharpened tip of the obturator, as is known in the art.

In another embodiment, it is contemplated that the DVDCS will include deformable portions exhibiting a substantially irregular, non-uniform or undulating profile. As is generally known in the art, radially deforming a cannula sleeve causes a resultant axial shortening of the instrument. This shortening not causes only an unwanted change in the overall axial dimension of the cannula, but may also result in the exposure of a penetrating device, if used in conjunction with a trocar assembly, for example, otherwise concealed within the cannula sleeve, thereby creating a potentially hazardous situation. In this embodiment, upon the radial expansion of the DVDCS, the irregular, non-uniform or undulating deformable portions will deform axially as well radially so as to compensate for any consequential degree of axial shortening, thereby allowing the DVDCS to maintain its overall length and continuously conceal the pointed tip of the penetrating device housed therein, thus preventing any inadvertent injury to the patient.

The irregular, non-uniform or undulating deformable portions of this embodiment also serve to substantially minimize retropulsion from the tissue site caused by the pressure exerted by insufflation gasses used during and throughout the procedure. The uneven surface of the DVDCS in this embodiment will resist the outward forces that may otherwise dislodge the DVDCS, as described above.

In any of the embodiments described herein, optionally, the system may further comprise a sleeve introducer adapted to facilitate introduction of the sleeve over a guidewire through the tissue tract. In some patients, utilizing the Seldinger or other conventional access techniques can prove difficult due the presence of scar tissue or other complicating factors. In such cases, significant axial force may be required to advance the sleeve distally over the guidewire. While the small profile of the introducer sleeve reduces the force necessary for introduction over the guidewire, in some cases it will be desirable to still further reduce that force. Such a reduction can be accomplished by providing a tapered distal tip on the sleeve. While this could be done by modifying the design of the DVDCS itself, it is more easily accomplished using a separate introducer sleeve having a tapered distal end and a lumen therethrough. The sleeve is configured to receive a guidewire through its lumen and to be received within the lumen of the deformable variable diameter cannula sleeve. By then placing the DVDCS over the sleeve introducer, the temporary assembly of the DVDCS and introducer can be inserted over the guidewire so that the tapered end of the introducer first advances through and deforms the tissue tract to reduce the necessary introduction force. After the distal end of the assembly reaches the desired location, either in a blood vessel or body cavity, the DVDCS may then be introduced over the assembly, i.e., the lumen of the DVDCS will pass over the exterior of the introducer. After deformation of the DVDCS is accomplished, the introducer and guidewire can then be removed from the access channel defined by the DVDCS.

Methods according to the present disclosure for establishing vascular or laparoscopic access comprise first forming a percutaneous tissue tract. Typically, the tissue tract is initially formed using a needle and guidewire according to conventional techniques, such as the first steps in the Seldinger access protocol. The DVDCS is then passed over the guidewire thereafter being positioned in the tissue tract such that the distal end of the DVDCS may be inserted into the target blood vessel or body cavity while the proximal end of the DVDCS remains outside the tissue tract. Thereafter, the DVDCS may be activated and allowed to deform.

These and other advantages and features of the present apparatus and method disclosed herein will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodiments of the disclosure and, together with the general description given above and the detailed description of the embodiments given below, serve to explain the principles of the present apparatus and method disclosed herein.

FIG. 4 is a perspective view of another embodiment of the present disclosure including a trocar assembly having a variable diameter cannula and an obturator positionable within the cannula;

FIG. 5 is a perspective view of the trocar assembly of FIG. 4 illustrating the obturator assembled within the cannula;

DETAILED DESCRIPTION OF THE SPECIFIC EMBODIMENTS

Figure 1:
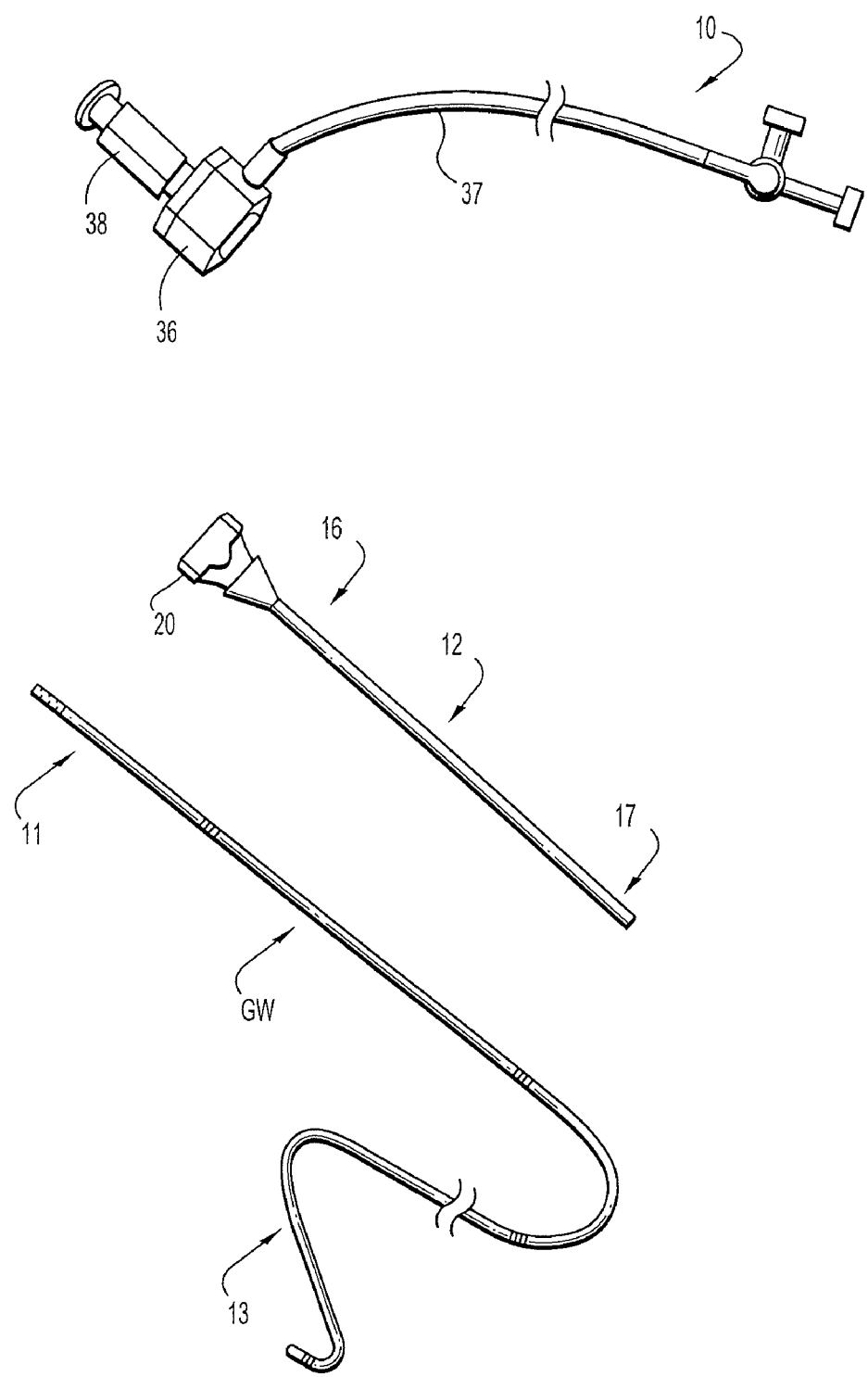
FIG. 1 illustrates a system including a deformable variable diameter cannula sleeve for use in establishing vascular access in accordance with the principles of the present disclosure.

Specific embodiments of the presently disclosed apparatus will now be described in detail with reference to the appended figures wherein like reference numerals identify similar or identical elements. In the figures and in the description, the term "proximal", as is traditional, will refer to the end of the apparatus or instrument of the present disclosure which is closest to the operator, while the term "distal" will refer to the end of the device or instrument which is furthest from the operator.

In each of the following embodiments, the deformation of the DVDCS may be triggered through the introduction of any of the aforementioned external stimuli including, but not limited to heat, an electrical current, a magnetic field or any such means capable of heating the memory material to its transitional temperature.

Referring to FIG. 1, a surgical portal system 10 for establishing percutaneous vascular access according to the principles of the present invention comprises a deformable variable diameter cannula sleeve (DVDCS) 12 and a guidewire GW with a proximal end 11 and a distal end 13. The DVDCS 12 comprises a radially deformable tubular body having a proximal end 16, a distal end 17 and an axial lumen extending from the proximal end 16 to the distal end 17. Usually, a handle 20 is provided at the proximal end of the body so that the sleeve can be manually held during use. The DVDCS 12 is composed, in whole or in part, of a mechanical memory material that facilitates change from a first diameter in a first, initial or un-activated configuration to a second diameter in a second, activated configuration. This change is caused by triggering the memory characteristics of the material through the introduction of an external stimulus, as described above.

The DVDCS 12 may be adapted for connection to a hemostatic valve assembly 36 and a side access tube 37 which permit perfusion or aspiration through the lumen thereof. The hemostatic valve assembly 36 may include a handle 38 and an internal lumen which permits introduction over the guidewire GW.

The guidewire GW may be a conventional vascular access guidewire, typically having a diameter of either 0.36 mm (0.014 in.) or 0.89 mm (0.035 in.), a length in the range from 35 cm to 100 cm, a proximal end 11 and a distal end 13.

Exemplary diameters for the DVDCS 12 in both the activated and un-activated configurations have been set forth above. Usually, the sleeve will have a length in the range from 3 cm to 30 cm, more usually from 10 cm to 25 cm. The exact dimensions of the sleeve will depend on the desired location and use of the DVDCS 12, whether laparoscopic or vascular in nature, or the like.

Figure 2A:
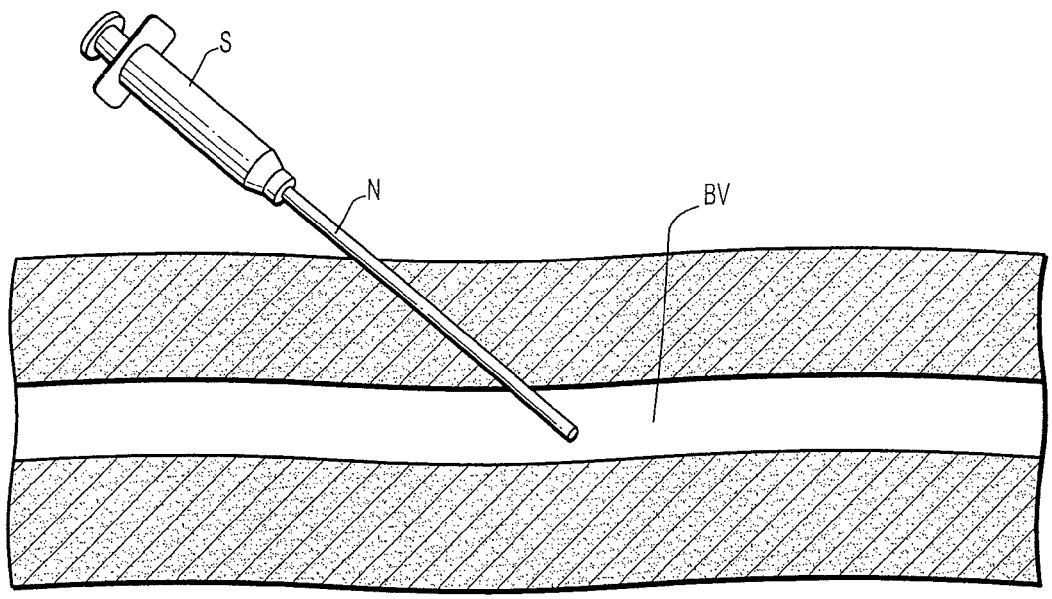
FIGS. 2A-2E illustrate use of the system of FIG. 1 in establishing vascular access to a target blood vessel according to a method of the present disclosure.
Figure 2B:
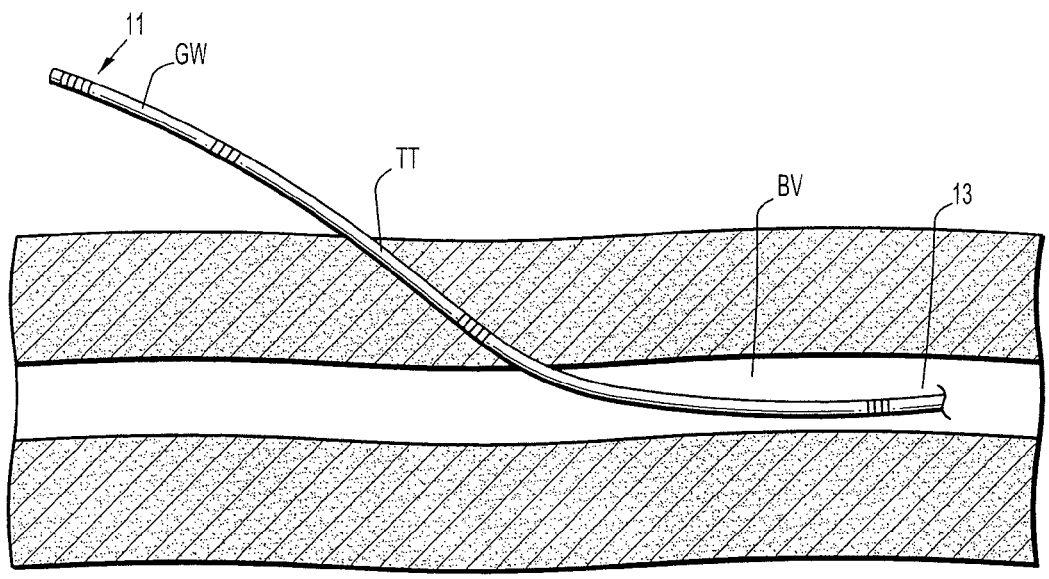
Figure 2C:
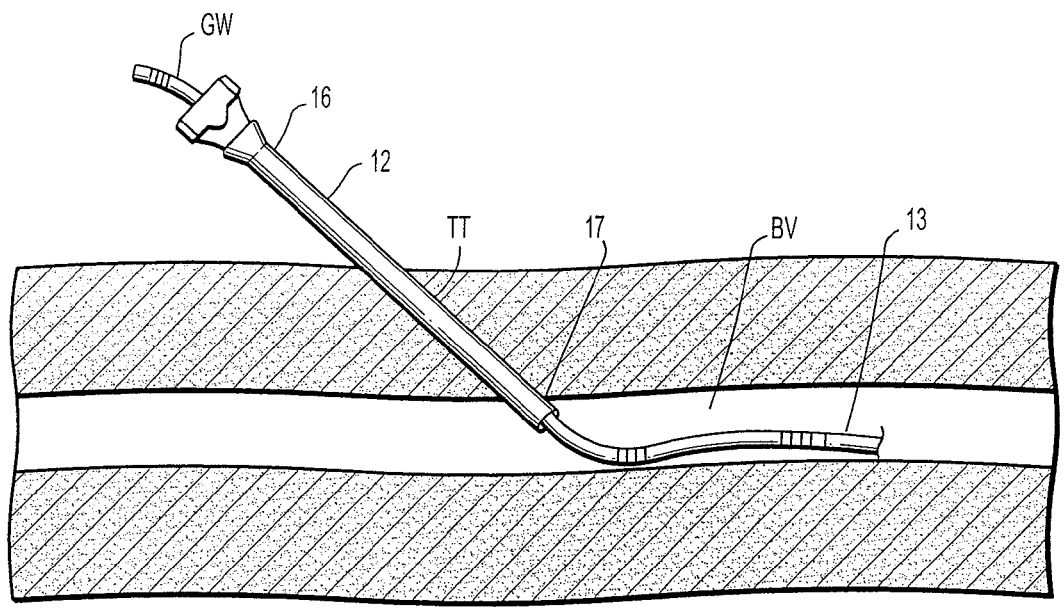
Figure 2D:
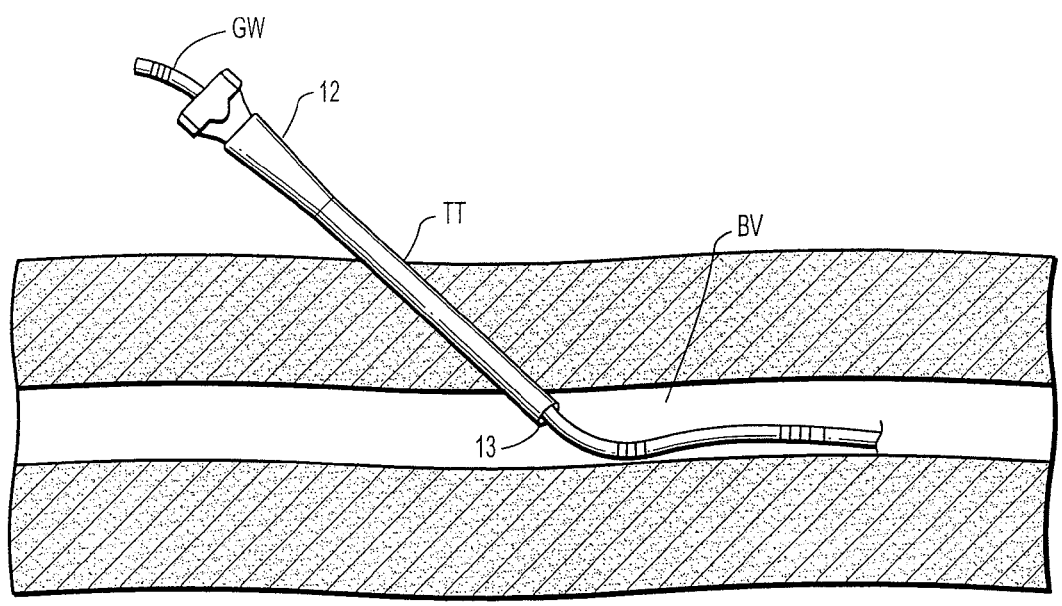
Figure 2E:
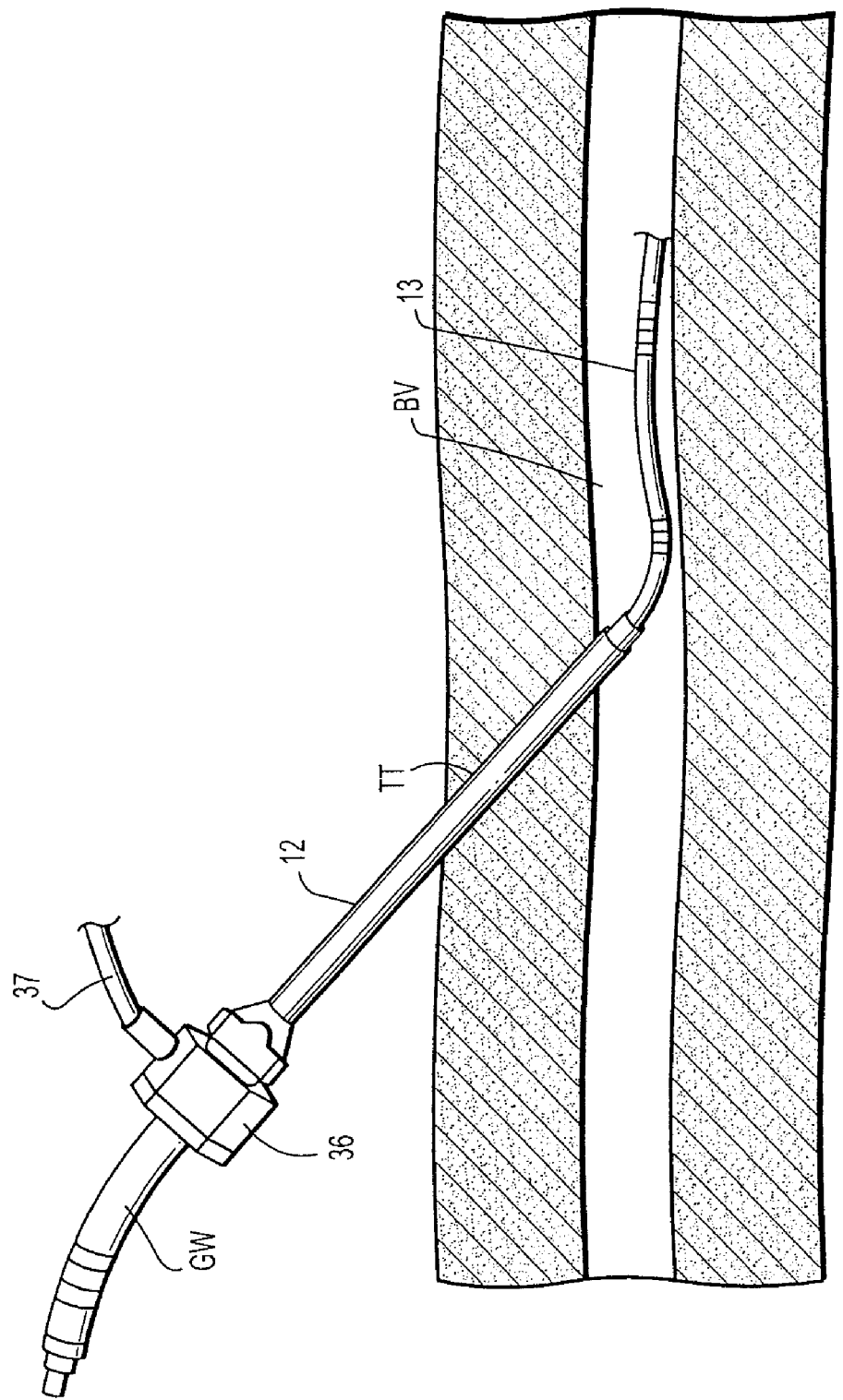

Referring now to FIGS. 2A-2E, use of the system 10 for accessing a blood vessel BV will be described. First, an initial tissue tract is formed using a needle N and a syringe assembly S, as shown in FIG. 2A. After insertion of the needle into the blood vessel BV is confirmed, typically by noting the flow of blood into the syringe S, the syringe may be removed and a guidewire GW placed through the needle into the blood vessel BV such that the distal end 13 of the guidewire GW lies therein. The needle N may then be withdrawn over the proximal end 11 of the guidewire GW, leaving the guidewire GW in place in tissue tract TT, as illustrated in FIG. 2B. The DVDCS 12 is then introduced over the guidewire GW so that its distal end 17 lies within the blood vessel BV, as shown in FIG. 2C. Upon insertion into the blood vessel BV, the DVDCS will be introduced to an external stimulus, as described above, until the transitional temperature of the memory material is realized. At this temperature, the dimensions of the DVDCS 12 will begin to change, as show in FIG. 2D and described above, transitioning from a first diameter in the un-activated configuration, to a second diameter in the activated configuration. As shown in FIG. 2E, upon reaching the pre-determined dimensions, DVDCS 12 will have established vascular access for performing any one of a wide variety of diagnostic or therapeutic procedures, as well described in the medical and patent literature.

Figure 3:
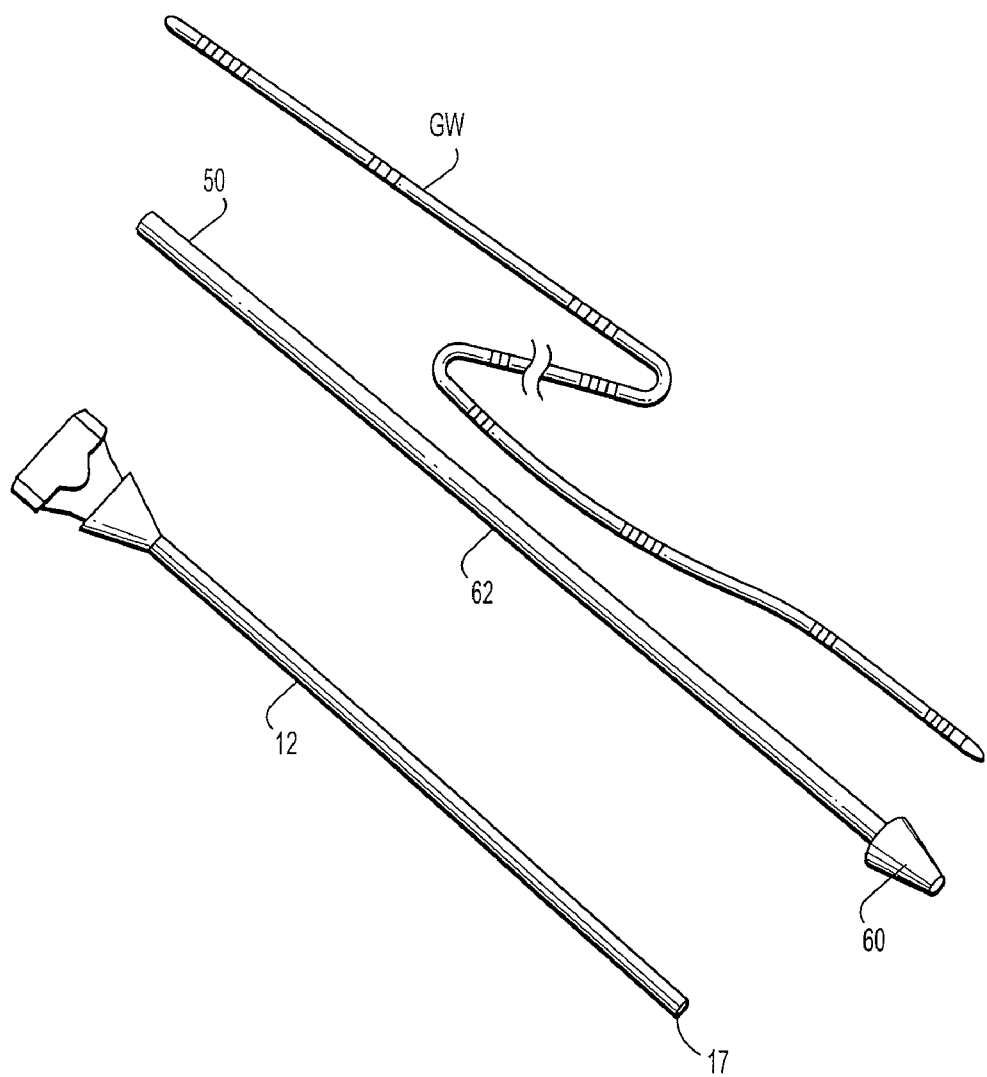
FIG. 3 illustrates a sleeve introducer which may be combined in an assembly with the system of FIG. 1, and optionally a guidewire, according to the present disclosure.

Referring now to FIG. 3, a sleeve introducer 50 may be combined with DVDCS 12 to form a surgical portal system intended for introduction through difficult tissue tracts, i.e., tissue tracts which might otherwise require excessive axial force to introduce DVDCS 12 according to the methods of the present invention. The sleeve introducer 50 comprises a tapered distal end 60, typically a conical element having a smaller diameter at its distal end and a larger diameter at its proximal end. The introducer 50 further comprises a shaft 62 extending proximally from the tapered distal end 60. The shaft will be a small tube, the distal end 60 and shaft 62 together defining a lumen which may be introduced over the guidewire GW. The outer diameter of the shaft 62 is selected so that it fits within the inner diameter of DVDCS 12. Preferably, the proximal end of the tapered distal end 60 will have a diameter which is the same as the outer diameter of the distal end 17 of DVDCS 12. In this way, the sleeve introducer 50 may be placed within the lumen of the DVDCS 12 to form an assembly having a tapered distal end which facilitates introduction over the guidewire GW.

Referring now to FIGS. 4 and 5, a trocar assembly constructed in accordance with a specific embodiment of the present disclosure, and designated generally by reference numeral 21, is shown. Trocar assembly 21 is particularly adapted for use in minimally invasive surgical procedures such as endoscopic or laparoscopic procedures. Generally, trocar assembly 21 includes two principal subassemblies, namely, cannula assembly 1000 and obturator assembly 100.

Cannula assembly 1000 may be any cannula assembly suitable for use in a laparoscopic surgical procedure. In a specific embodiment, cannula assembly 1000 includes cannula housing 1002 and cannula sleeve 1004 extending from the cannula housing 1002. Cannula sleeve 1004 is fabricated, either wholly or in part, from the shape memory material described above in accordance with the present invention. Cannula assembly 1000 may include an internal seal such as a duck-bill valve or other zero closure valve (not-shown)

adapted to close in the absence of a surgical instrument to prevent passage of insufflation gases through the cannula assembly 1000.

Obturator assembly 100 includes obturator housing 102, obturator shaft 104 defining obturator axis "x" and extending distally from the housing 102 and obturator shield 106 coaxially mounted about the obturator shaft 104. In general, in a first preferred mode of operation, obturator shield 106 defines a distal shield nose 206 which may be used to enter, penetrate or pass through tissue. Alternatively, in a second mode of operation, obturator shield 106 may be adapted to retract in a proximal longitudinal direction to expose a cutting blade disposed at the distal end of the obturator shaft 104.

Trocar assembly 21 may also include a seal assembly 2000 which is preferably releasably mounted to cannula housing 1002. Means for releasably connecting seal assembly 2000 to cannula housing 1002 may include a bayonet coupling, threaded connection, latch, friction fit, tongue and groove arrangements, snap-fit, etc. Seal assembly 2000 includes at least one internal seal (not shown) adapted to form a fluid tight seal about an instrument inserted therethrough. One suitable seal may be the fabric seal disclosed in commonly assigned U.S. Pat. No. 6,702,787 to Racenet et al., the entire contents of which are incorporated herein by reference. The seal disclosed in the Racenet '787 patent may be a flat septum seal having a first layer of resilient material and a second fabric layer juxtaposed relative to the first layer. Further details of the seal may be ascertained by reference to the '787 patent. Seal assembly 2000 may or may not be a component of cannula assembly 1000. For example, the seal assembly may be a separate, removable assembly. In the alternative, the seal assembly may comprise an integral part of the cannula assembly 1000 and not be removable.

Figure 6:
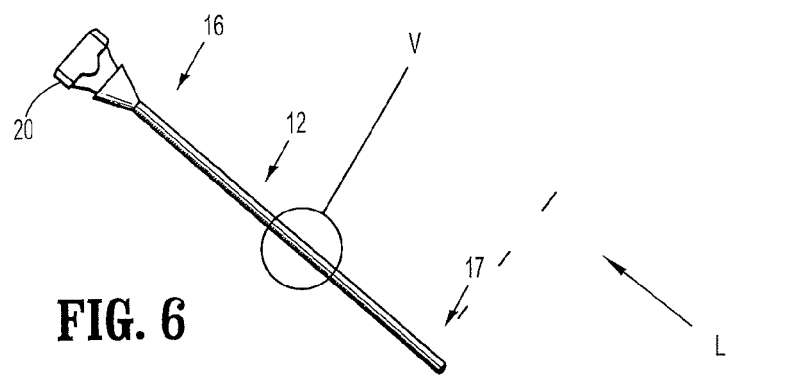
FIG. 6 is a perspective view of another embodiment of the present disclosure including a cannula having or undulating portion.
Figure 6A:
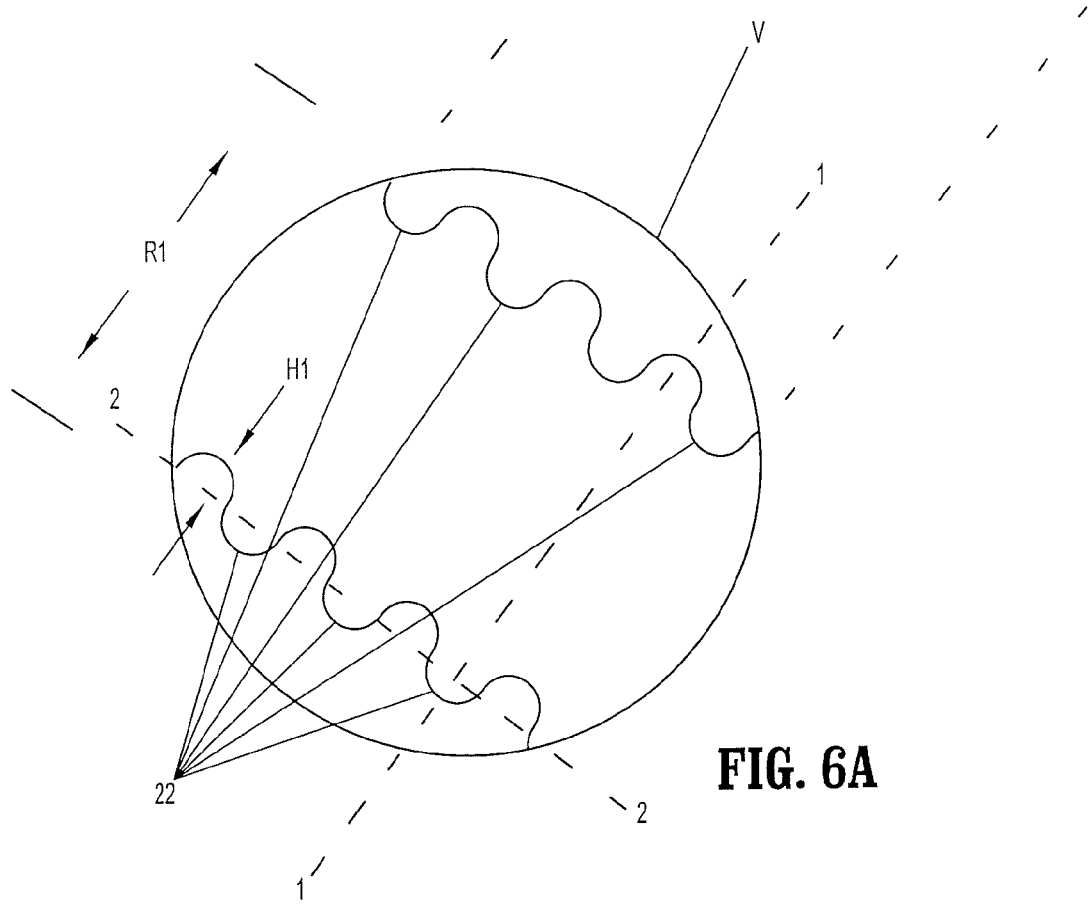
FIG. 6A is an enlarged isolated view of the area of detail identified in FIG. 6 illustrating the undulating portion of the cannula in an initial condition.

Referring to FIGS. 6-6A, a specific embodiment of the present disclosure employing at least one substantially irregular, non-uniform or undulating portion is illustrated. FIG. 6 illustrates the DVDCS 12, generally, and section "V" focuses on a portion of the DVDCS 12. FIG. 6A is a close-in view of section "V" in which deformable portions 22 of the DVDCS 12 are illustrated. As appreciated, FIG. 6A depicts the DVDCS 12 and the deformable portions 22 in the un-activated or initial condition described above, that is, prior to deformation. As seen in FIG. 6A, prior to the radial deformation of the DVDCS 12, along axis 1-1, the deformable portions 22 are in an un-activated or "compressed" state, exhibiting a substantially irregular, non-uniform or undulating profile. Furthermore, in the un-activated state, the DVDCS 12 exhibits axial dimension "L".

The substantially irregular, non-uniform or undulating profile of the deformable portions in the un-activated state allow for the incorporation of additional material that will enable the DVDCS to deform axially, as well as radially upon activation, as described above. These sections further substantially minimize retropulsion from the tissue site caused by the pressure exerted by insufflation gasses used during and throughout the procedure, as described above. Accordingly, in this embodiment, the substantially irregular, non-uniform or undulating profile of the deformable portions of the DVDCS will resist outward forces that may otherwise dislodge the DVDCS, as described above.

Figure 6B:
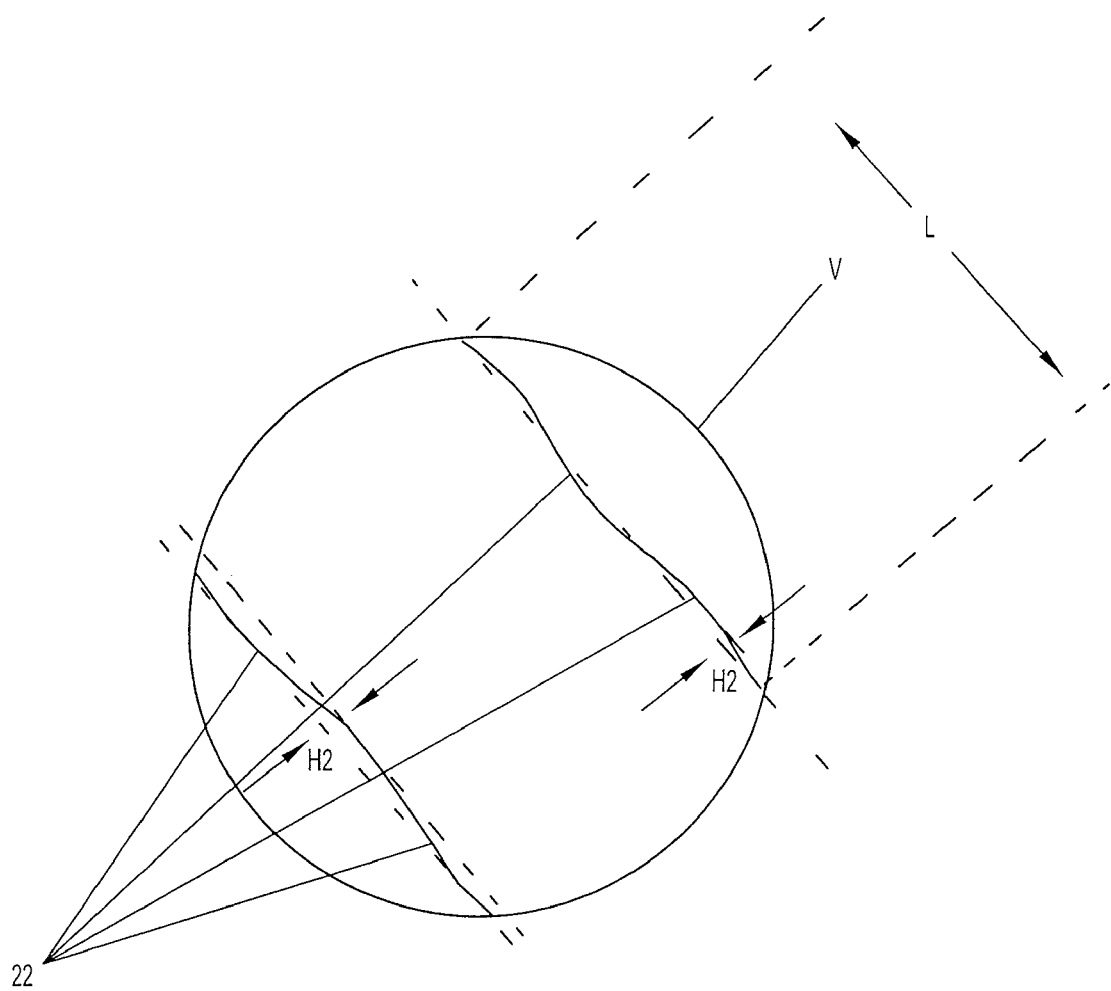
FIG. 6B is an enlarged view similar to the view of FIG. 7 illustrating the undulating portion in an activated condition.

Referring now to FIGS. 6A and 6B in concert, during radial deformation, the DVDCS 12 will transition from a first radial dimension R1, where deformable portions 22 exhibit a first radial dimension H1, as seen in FIG. 6A, to a second radial dimension R2, where the deformable portions 22 exhibit a second radial dimension H2, as seen in FIG. 6B. Accordingly, as the DVDCS 12 deforms radially along axis 1-1, so too will deformable portions 22. In addition, however, deformable portions 22 will also deform axially along axis 2-2. This deformation allows the DVDCS 12 to substantially maintain its overall length "L", thereby preventing any substantial axial shortening. FIG. 6B depicts the DVDCS 12 following the deformation process. As indicated in that figure, the DVDCS 12 and deformable portions 22 have reconfigured to now exhibit radial dimensions R2 and H2, respectively. Axial dimension "L" of the DVDCS 12, however, remains substantially unchanged. As discussed above, it is contemplated that R2 may be of greater or lesser dimensions than R1. Likewise, it is contemplated that H2 may be of greater or lesser dimension than H1, dependent upon the application in which the DVDCS is employed. It is further contemplated that the expandable portions may be exhibit sinusoidal, triangular or any such configuration so long as the maintenance of the overall axial dimension of the DVDCS upon radial deformation is provided for.

Figure 7:
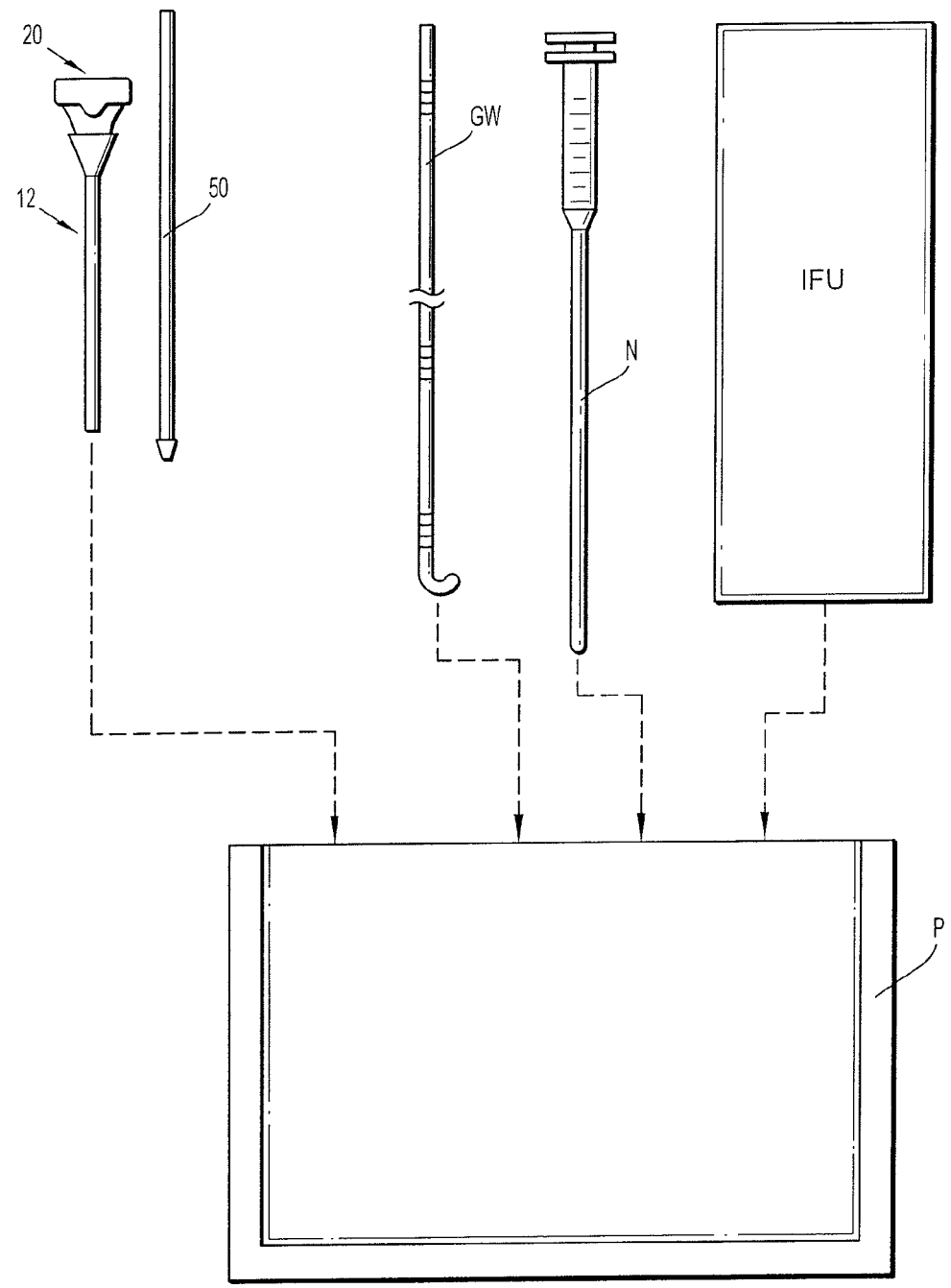
FIG. 7 illustrates a kit constructed in accordance with the principles of the present disclosure.

Referring now to FIG. 7, kits according to the present invention will comprise at least one DVDCS 12 with a handle 20 together with instructions for use (IFU) setting forth a method according to the principles of the present invention. The kits may optionally further comprise a guidewire GW, a sleeve introducer 50 and/or a needle N, and all kit components will typically be packaged together in a box, tray, tube, pouch or other conventional medical device package P. The kit components which are employed in the medical procedure will typically be maintained within sterile packaging, with individual components being packaged either together or separately in different sterile containers. Usually, even when packaged in separate sterile containers, all components of the kit will be placed together within a common package. The instructions for use may be provided on a separate printed sheet, such as a conventional package insert, or may be printed in whole or in part on other portions of the packaging or the device itself.

Figure 8:
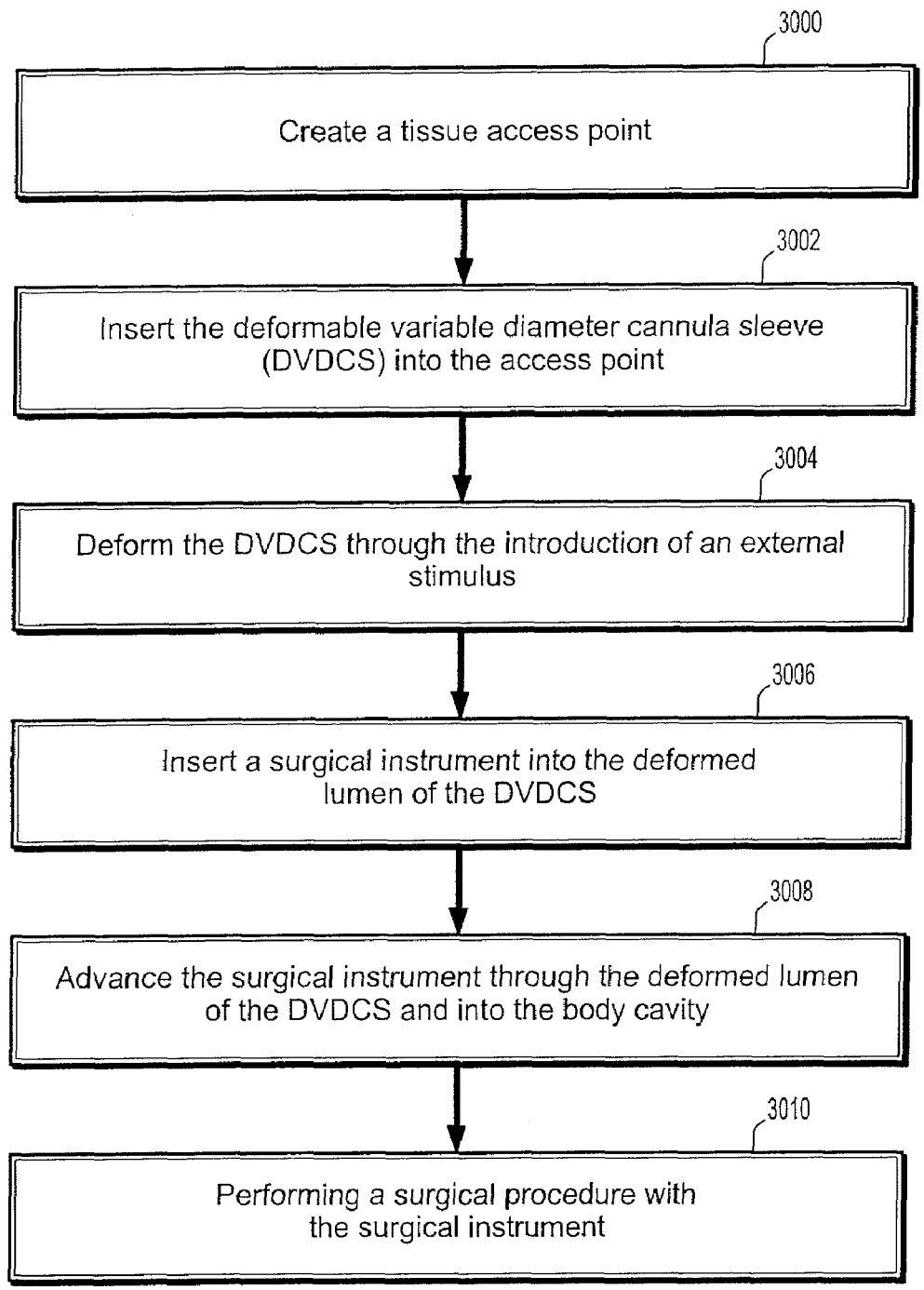
FIG. 8 is a flow diagram illustrating a methodology for using the system in accordance with the principles of the present disclosure.

FIG. 8 illustrates a methodology for performing a surgical procedure according to the principles of the present disclosure. The method incorporates the steps of:

1) creating a tissue access point (Step 3000) with a trocar, needle or the like;
2) inserting the DVDCS into the access point (Step 3002);
3) deforming the DVDCS through the introduction of an external stimulus such as body head, magnetic means, or RF energy (Step 3004) whereby the DVDCS moves from the initial condition to the activated condition, e.g., from a small diameter to a large diameter;
4) inserting a surgical instrument into the deformed lumen (Step 3006);
5) advancing the surgical instrument through, the deformed lumen of the DVDCS and into the body cavity (Step 3008); and
6) performing a surgical procedure with the surgical instrument.(Step 3010)

While the above is a complete description of the preferred embodiments of the disclosure, various alternatives, modifications, and equivalents may be used. Therefore, the above description should not be taken as limiting the scope of the apparatus and method disclosed herein and defined by the appended claims.

What is claimed is:

1. A surgical portal which comprises:
an elongate portal member dimensioned to access tissue to provide access to an underlying tissue site, the elongate portal member defining proximal and distal ends and a longitudinal axis, the elongate portal member defining an axial lumen adapted for reception of a surgical object, the elongate portal member including at least one radially deformable portion comprising a shape memory material and having an undulating configuration with sections extending in opposite directions relative to the longitudinal axis, and positioned in adjacent relation along the longitudinal axis, the at least one radially deformable portion adapted to move from an initial condition, wherein the at least one radially deformable portion has a first radial dimension and the adjacent sections are out of alignment with the longitudinal axis, to an activated condition, wherein the at least one radially deformable portion has a second radial dimension different from the first radial dimension and the adjacent sections are in substantial alignment with the longitudinal axis, whereby an overall axial length of the elongate portal member remains substantially constant during movement of the at least one radially deformable portion from the initial condition to the activated condition, the at least one radially deformable portion being moved from the initial condition to the activated condition upon exposure to an external stimulus.

2. The surgical portal system of claim 1 wherein the shape memory material is adapted to move from the initial condition to the activated condition upon exposure to heat.

3. The surgical portal system of claim 2 wherein the shape memory material is adapted to move from the initial condition to the activated condition upon exposure to the heat generated by the patient's body.

4. The surgical portal system of claim 1 wherein the shape memory material is adapted to move from the initial condition to the activated condition upon exposure to a magnetic field.

5. The surgical portal system of claim 1 wherein the shape memory material is adapted to move from the initial condition to the activated condition upon exposure to an RF source.

6. The surgical portal system of claim 1 wherein the diameter of the at least one radially deformable portion is adapted to move from the initial condition to the activated condition in proportionate relation to the temperature of the elongate portal member.

7. The surgical portal system of claim 1 wherein the shape memory material is selected from a group consisting of a titanium-nickel alloy, a titanium-nickel-cobalt alloy, a ferromagnetic shape memory alloy, and a two-way shape memory material.

8. The surgical portal system of claim 1 wherein the elongate portal member is a cannula adapted to access the abdominal cavity.

9. The surgical portal system of claim 1 wherein the elongate portal member is adapted for accessing vascular tissue.

10. The surgical portal system of claim 1 wherein the elongate portal member includes at least one axially expandable portion.

11. The surgical portal system of claim 1 wherein the at least one radially deformable portion includes at least one substantially non-uniform section defining at least one portion with a first radial dimension in the initial condition and a second radial dimension in the activated condition.

12. The surgical portal system of claim 1, wherein the at least one radially deformable portion includes an outer surface having an irregular contour.

13. A surgical method for performing a procedure, comprising the steps of:
creating a tissue access point through puncture of a tissue wall;
inserting an elongate portal member into the access point, the elongate portal member defining a longitudinal axis, and having an axial lumen adapted for the reception of a surgical object, the elongate portal member including at least one radially deformable portion comprising a shape memory material and having an undulating configuration with sections extending in opposite directions relative to the longitudinal axis, and positioned in adjacent relation along the longitudinal axis, the at least one radially deformable portion adapted to move from an initial condition, wherein the at least one radially deformable portion has a first radial dimension and the adjacent sections are out of alignment with the longitudinal axis, to an activated condition, wherein the at least one radially deformable portion has a second radial dimension different from the first radial dimension and the adjacent sections are in substantial alignment with the longitudinal axis, the at least one radially deformable portion being moved from the initial condition to the activated condition upon exposure to an external stimulus;
deforming the elongate portal member through the introduction of an external stimulus, whereby the at least one radially deformable portion moves to the activated condition, and the adjacent sections of the at least one radially deformable portion are substantially aligned with the longitudinal axis, whereby an overall axial length of the elongate portal member remains substantially constant;
inserting a surgical instrument into the deformed lumen of the elongate portal member;
advancing the surgical instrument through the deformed lumen of the elongate portal member and into the body cavity; and
performing a surgical procedure with the surgical instrument.

14. The surgical portal system of claim 13, wherein the undulating configuration of the at least one radially deformable portion includes a first section extending radially inward towards the longitudinal axis, and a second section extending radially outward away from the longitudinal axis, wherein the first and second sections are positioned adjacent each other.

15. A surgical portal comprising:
an elongate portal member defining a longitudinal axis, and being dimensioned to access tissue to provide access to an underlying tissue site, the elongate portal member including at least one radially deformable portion comprising a shape memory material, at least a section of the deformable portion having a configuration undulating along the longitudinal axis. the at least one radially deformable portion being adapted to move from an initial condition, wherein the at least one radially deformable portion defines a first radial dimension and a first length, to an activated condition, wherein the at least one radially deformable portion defines a second radial dimension different than the first radial dimension and a second length different than the first length such that an overall axial length of the elongate portal member remains substantially constant upon movement of the at least one radially deformable portion from the initial condition to the activated condition, the at least one radially deformable portion being configured, dimensioned, and adapted to transition from the initial condition to the activated condition upon exposure to an external stimulus.

16. The surgical portal system of claim 15, wherein the undulating configuration of the at least one radially deformable portion including a first section extending radially inward towards the longitudinal axis, and a second section extending radially outward away from the longitudinal axis, wherein the first and second sections are positioned adjacent each other.

17. The surgical portal of claim 15, wherein the at least one radially deformable portion includes an outer surface having an irregular contour.

* * * * *